US009445934B2

(12) United States Patent
Ugarte

(10) Patent No.: US 9,445,934 B2
(45) Date of Patent: Sep. 20, 2016

(54) CATHETER COLLECTION AND DRAINAGE DEVICE AND SYSTEM

(71) Applicant: Roland Rene Ugarte, Wayzata, MN (US)

(72) Inventor: Roland Rene Ugarte, Wayzata, MN (US)

( * ) Notice: Subject to any disclaimer, the term of this patent is extended or adjusted under 35 U.S.C. 154(b) by 0 days.

(21) Appl. No.: 14/929,625

(22) Filed: Nov. 2, 2015

(65) Prior Publication Data

US 2016/0051395 A1     Feb. 25, 2016

Related U.S. Application Data

(63) Continuation-in-part of application No. PCT/US2014/036315, filed on May 1, 2014.

(60) Provisional application No. 61/818,627, filed on May 2, 2013.

(51) Int. Cl.
| *A61F 5/44* | (2006.01) |
| *A61J 1/10* | (2006.01) |
| *A61F 5/455* | (2006.01) |
| *A61F 5/453* | (2006.01) |
| *A61M 25/00* | (2006.01) |

(52) U.S. Cl.
CPC .......... *A61F 5/4556* (2013.01); *A61F 5/4404* (2013.01); *A61F 5/4405* (2013.01); *A61F 5/4408* (2013.01); *A61F 5/453* (2013.01); *A61J 1/10* (2013.01); *A61M 25/0017* (2013.01)

(58) Field of Classification Search
CPC .... A61F 5/4556; A61F 5/4408; A61F 5/453; A61F 5/4404; A61F 5/4405; A61F 5/44; A61M 25/0017; A61M 1/0017; A61M 1/167; A61M 1/0011; A61J 1/10; A61J 1/1475; A61J 1/1481; A61J 1/1487; A61J 1/2048
See application file for complete search history.

(56) References Cited

U.S. PATENT DOCUMENTS

| 1,788,709 | A | * | 1/1931 | De Spain | F04F 10/00 137/140 |
| 3,721,243 | A | * | 3/1973 | Hesterman et al. | A61F 5/453 604/185 |
| 3,926,233 | A | * | 12/1975 | Brendling | A61F 5/44 383/38 |
| 4,084,593 | A | * | 4/1978 | Jarund | A61F 5/4404 128/DIG. 25 |
| 4,138,036 | A | * | 2/1979 | Bond | B65D 77/06 222/105 |
| 4,161,179 | A | * | 7/1979 | Abramson | A61M 1/0011 128/DIG. 24 |

(Continued)

FOREIGN PATENT DOCUMENTS

| WO | 99/23978 | 5/1999 |
| WO | 2014/179536 | 11/2014 |

OTHER PUBLICATIONS

Search Report and Written Opinion from corresponding International Application No. PCT/US2014/036315, dated Nov. 8, 2014 (12 pages).

(Continued)

*Primary Examiner* — Adam Marcetich
(74) *Attorney, Agent, or Firm* — Kagan Binder, PLLC

(57) ABSTRACT

A urine collection and drainage device and system adapted to facilitate drainage for patients to that prefer to stay standing during drainage and avoid removal of clothing near the collection bag. A collection vessel is designed to be secured to a user's waist and leg and allows for quick drainage with low initial compression. Drainage can also be accomplished for handicapped patients that have challenges getting out of bed or a wheelchair.

24 Claims, 8 Drawing Sheets

(56) References Cited

U.S. PATENT DOCUMENTS

| | | | |
|---|---|---|---|
| 4,449,971 A | | 5/1984 | Cawood |
| 4,466,888 A | * | 8/1984 | Verkaart ............. A61M 1/0001 210/232 |
| 4,695,279 A | | 9/1987 | Steer |
| 4,729,188 A | * | 3/1988 | Cheng .................... A01G 31/06 47/14 |
| 4,846,816 A | | 7/1989 | Manfredi |
| 4,961,419 A | | 10/1990 | Tribble et al. |
| 5,002,541 A | | 3/1991 | Conkling et al. |
| 5,032,118 A | | 7/1991 | Mason |
| 5,053,027 A | | 10/1991 | Manfredi |
| 5,466,250 A | * | 11/1995 | Johnson, Jr. .............. A61F 5/34 601/15 |
| 5,618,277 A | | 4/1997 | Goulter |
| 5,975,351 A | * | 11/1999 | DeLacerda ......... B65B 69/0075 222/1 |
| 6,007,521 A | | 12/1999 | Bidwell et al. |
| 6,045,542 A | | 4/2000 | Cawood |
| 6,302,607 B1 | * | 10/2001 | Burrowes ............. A45D 19/02 132/148 |
| 6,352,526 B1 | | 3/2002 | Cawood |
| 6,471,680 B1 | | 10/2002 | Cawood |
| 6,551,293 B1 | | 4/2003 | Mitchell |
| 6,682,511 B2 | | 1/2004 | Besoyan |
| 6,736,803 B2 | | 5/2004 | Cawood |
| 7,066,918 B2 | | 6/2006 | Charles |
| 7,160,276 B2 | | 1/2007 | Bruns |
| 7,517,343 B2 | | 4/2009 | Tanghoj et al. |
| 7,931,630 B2 | | 4/2011 | Nishtala et al. |
| 8,002,766 B2 | | 8/2011 | Tanghoj et al. |
| 8,608,718 B1 | * | 12/2013 | Patterson-Young .. A61F 5/4408 604/345 |
| 2003/0040708 A1 | * | 2/2003 | Rogers ................. A61M 5/148 604/135 |
| 2003/0073977 A1 | | 4/2003 | Charles |
| 2003/0204176 A1 | | 10/2003 | Besoyan |
| 2005/0251100 A1 | | 11/2005 | Charles |
| 2006/0079853 A1 | * | 4/2006 | Christensen ........ A61M 1/0001 604/317 |
| 2007/0005031 A1 | | 1/2007 | Charles |
| 2007/0235454 A1 | * | 10/2007 | Woodruff ............... A47K 3/001 220/495.01 |
| 2008/0140033 A1 | * | 6/2008 | Burgess .................... A61F 5/44 604/322 |
| 2008/0234652 A1 | * | 9/2008 | McCarthy .......... A61B 19/0248 604/410 |
| 2010/0286667 A1 | * | 11/2010 | Paz ................... A61M 25/0017 604/544 |
| 2012/0288572 A1 | * | 11/2012 | Kugelmann .......... A61K 1/2093 424/678 |
| 2013/0049356 A1 | * | 2/2013 | Pittet .................... A61J 1/1475 285/125.1 |

OTHER PUBLICATIONS

International Preliminary Report on Patentability from corresponding International Application No. PCT/US2014/036315, dated Nov. 3, 2015 (9 pages).

* cited by examiner

CATHETER COLLECTION AND DRAINAGE DEVICE AND SYSTEM

CLAIM OF PRIORITY TO INTERNATIONAL APPLICATION

This application is a continuation in part of and claims priority to, and the benefit of, International Application PCT/US2014/036315, with an international filing date of May 1, 2014, now soon to be abandoned. This application also claims priority to and the benefit of U.S. Provisional Patent Application No. 61/818,627, filed May 2, 2013 and entitled "A CATHETER COLLECTION AND DRAINAGE DEVICE AND SYSTEM" which application is incorporated herein by reference in its entirety.

FIELD AND BACKGROUND OF THE INVENTION

The invention relates generally to a device and system for bodily waste collection and drainage.

Currently, patients dealing with urinary incontinence and that are catheter users tend to fall into one the following categories: 1) patients that use self-intermittent catheters where no urine collection or drainage bags are necessary; 2) patients with indwelling or Foley catheters who rely on some type of drainage/urine collection bag; and 3) male patients who wear an external or condom catheter (or sheath catheter) that also require a urine drainage bag or collection system. Patients, male or female, that have to rely on some form of collection or drainage bag are faced with a number of challenges such as portability of such a collection bag without creating wardrobe issues and ease of drainage of the collection bag, especially in public restrooms, just to name a few.

The storage or collection bags currently provided usually attach to the body, customarily to the leg or thigh, by one or two straps, and is connected to either the indwelling catheter or the sheath/condom catheter (or catheter tip) portion by a plastic tube. One challenge is that, as urine collects in the storage bag, its increased weight sometimes causes the connections to disengage or the condom/internal catheter to be pulled loose from the male penis or from the female's urethra. Another challenge is that there are various sources of potential leakage, i.e., at any of the connection points between the collection bag and an interconnection tube between the bag and the indwelling catheter or seal leaks in the collection bag due to a pressure spike. The result being frequent spillage, leaking, soiling, and embarrassment to the user. Another challenge is that this ungainly arrangement is a barrier to many normal activities, such as running, aerobics, and light physical work.

Further problems relate to the emptying of the bag of urine, as well with the attachment of the storage bag to the leg or thigh. Either the user has to undress in order to empty the bag, or he has to wear trousers loosely-fitting enough to allow a user to roll up the trouser leg to get at it. Both methods are cumbersome and require the user to take much longer to use a toilet or urinal than is normal. Moreover, if a man has to drain the storage bag in a public urinal, he is faced with an embarrassing situation. Another disadvantage is that there is insufficient support for the storage or collection bag beyond the straps fitted around the leg, which are both tight and uncomfortable yet insecure (i.e., the straps tended to restrict blood circulation yet could not always prevent the storage unit from slipping down the leg). Also, the storage bag prevents the user from wearing ordinary, closely-fitted street clothes, because the collection bag outline could show through and because the trouser leg could not be rolled up high enough to allow the user to access the bag. The drain valve on these storage bags also presents problems, whether the pull-out plug or the screw-off cap. Men with shaky or arthritic hands or with neurologic pathologies (MS, Parkinson's disease, stroke, etc.) might have difficulty replacing a plug or screwing a cap off and on. Some users also tended to get urine on their hands while draining the device.

Further, the disabled have particular difficulty in handling such collection bags. The problems of the various types of drainage catheters are so great that some patients are unable to cope with them. Hence, in these instances the only alternative is to wear bulky and embarrassing adult diapers or to refuse to go out in public at all. For all these reasons, the urine-incontinent man or woman is often severely handicapped in both his economic and social life.

In one prior art device, Cawood discloses in U.S. Pat. No. 4,449,971 an abdominally located urine collection bag that is connected to a catheter protruding up from the patient's urethra (in this case, the patient's penis), such that the patient's urine needs to travel upwards against gravity to be deposited in the abdominally located collection bag. As taught therein, this collection bag system depends on the patient's bladder detrusor muscle tone and intraperitoneal pressures exerted upon the bladder of the catheterized ambulatory patient so as to cause urine to flow from the bladder to a level as high as 10 centimeters or more above the distal tip of the catheter within the patient. The collection bag is carried by a waistband or belt and is worn over the patient's abdomen and the bag disclosed in the Cawood patent has a short valve-equipped drain tube that extends downwardly from the bag when the contents are to be drained and that may be folded upwardly and inserted into a pocket provided by the bag when the drain tube is not in use. A challenge with the Cawood system is that not all patients have sufficient bladder strength to force their urine up against gravity to an abdominally located collection bag (especially if a patient has a neurogenic bladder, which provides minimal to no bladder contractions). Further, this collection bag will require more loose fitting clothes to accommodate the device and can create leakage issues if the user has to bend over at the waist just to pick something up.

Cawood in U.S. Pat. No. 6,471,680 also discloses an abdominally-worn collection bag that includes a long coiled extension tube connected to the drain tube and drain tube connector to allow the patient to drain the urine contents directly into a toilet bowl as shown in the '680 patent. The extension tube has the challenge of having to be uncoiled and then re-coiled and strapped into the front face of this collection bag when trying to empty the urine bag. This requires manual dexterity in managing the tube, partially undressing to manage the long tube and some hygienic challenges in cleaning the tube after each use and ensuring that it is completely empty before recoiling.

Therefore, there is a need for a urine or body waste collection and drainage device and system that is simple to use and facilitates ease of drainage for the mobile and active patient without all of the complexities of the aforementioned prior art devices.

SUMMARY OF THE INVENTION

Various embodiments of a bodily waste collection and drainage device and system described herein provide advantages over the prior art such as ease of use, ease of drainage or disposal of contents, accommodates to the user's body and clothing, and longer use due to robust support system. It would further be advantageous to have a collection and drainage device for both men and women that is easy to use and more sanitary then current options available on the market.

In one example embodiment, a bodily waste collection and drainage system is comprised of a collection bag, a support band or strap adapted to support the bag on the user, an inlet configured to be coupled to a catheter of a user and an outlet having a drainage tube member passing there through for ease of drainage or emptying of the collection bag. The drainage tube member includes a valve for turning on or off the outflow of bodily waste from the collection bag. In a related embodiment, the collection system is configurable for use in colostomy applications or for other drainage applications for the human body.

In another example embodiment, a catheter device accessory assembly for urine collection of a patient is provided that includes a urine collection vessel having an upper portion and a lower portion and an inlet port disposed on the urine collection vessel and configured to be coupled to a connector, the connector adapted to be connected to a catheter device. The device accessory also includes an outlet port disposed on the upper portion of the urine collection vessel and disposed separate and above the inlet port, the outlet port having an external side and an internal side. The device accessory also includes a drainage tube assembly comprising an external tube portion and an internal tube portion, the external tube portion coupled to the external side of the outlet port and adapted to extend away from the collection vessel for drainage, the internal tube portion coupled to the internal side of the outlet port and adapted to extend from the outlet port and internally into the lower portion of the collection vessel, a distal end of the internal tube portion in operative contact with a floor or bottom of the collection vessel, wherein the internal tube has at least one hole in a sidewall of the tube spaced from the distal end of the internal tube portion. In addition, the collection vessel is configured to be emptied through said drainage tube assembly upon initial compression by the patient of the lower portion of the collection vessel, thereby commencing a siphoning action. In a related embodiment, the urine collection vessel is adapted to be emptied through the drainage tube and with compression by the patient when in a standing position. In yet another related embodiment, a waistband attachment assembly is included which is adapted to support the collection vessel on a user's body such that the inlet port is adjacent a proximal end of a catheter located in a patient's urethra. The device accessory further includes a leg band member configured to secure the collection vessel to a patient's leg and includes a spacing gap member located between the waistband assembly and the upper portion of the collection vessel, the spacing gap configured to house the non-extended external tube portion.

In yet another example embodiment, a catheter accessory device for collecting urine from a patient includes a urine collection vessel having an upper and lower portions and configured to be supported by the patient's waist or leg and an inlet port coupled to the urine collection vessel the inlet port having a connector coupled to a catheter. The accessory device also includes an outlet port disposed in the upper portion of and coupled to the urine collection vessel, the outlet port coupled to a drainage tube member that is adapted to extend above the inlet port and away from the collection vessel, an internal portion of the drainage tube member extending to a bottom of the urine collection vessel and an external portion of the drainage tube member comprising a valve for selectively draining the urine collection vessel. The accessory device also includes a drain valve coupled to the bottom of the urine collection vessel and coupled at another end with the internal portion of the drainage tube member, the internal portion of the drainage tube being disposed in an upright configuration from the drain valve and including at least one hole in a sidewall near the drain valve. The urine collection vessel is also adapted to be emptied through the drainage tube member when the patient is in a standing position by initially compressing the vessel until a siphoning action commences.

In yet another related embodiment, a front panel of the collection vessel of the catheter device assembly is configured to be compressed against a stiffened rear panel of the collection vessel to improve collection vessel drainage. In this example embodiment, the stiffened rear panel is either a thicker rear collection vessel or a rigid/semi-rigid backing plate or panel disposed next to the rear panel of the collection vessel.

In yet another example embodiment, a bodily fluid collection system for use by a patient including a collection vessel configured to have an inlet port and an outlet port, the inlet port disposed proximate to a patient's drainage orifice when the collection system is in use, wherein drainage from the orifice occurs gravitationally. The system also includes a bodily conduit member configured to be coupled to said inlet port and coupled to the patient's drainage orifice and a drainage conduit member configured to be coupled to the outlet port and adapted to extend from the collection vessel for drainage of the collection vessel, wherein a portion of the drainage conduit member extends internally into the collection vessel below the inlet port and wherein a distal end of said drainage conduit member is in operative contact with a floor or bottom of the collection vessel, the drainage conduit member having at least one hole in a sidewall of the tube spaced from the distal end of said drainage conduit member; wherein said collection vessel is configured to be emptied through said drainage conduit member upon initial compression by the patient of the lower portion of the collection vessel, thereby commencing a siphoning action.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION OF THE INVENTION

Following below are more detailed descriptions of various embodiments of the invention described herein. In particular, the various embodiments disclosed herein describe a urine collection and drainage device for patients that prefer to drain their urine collection bag while in a standing position. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Figure 1:
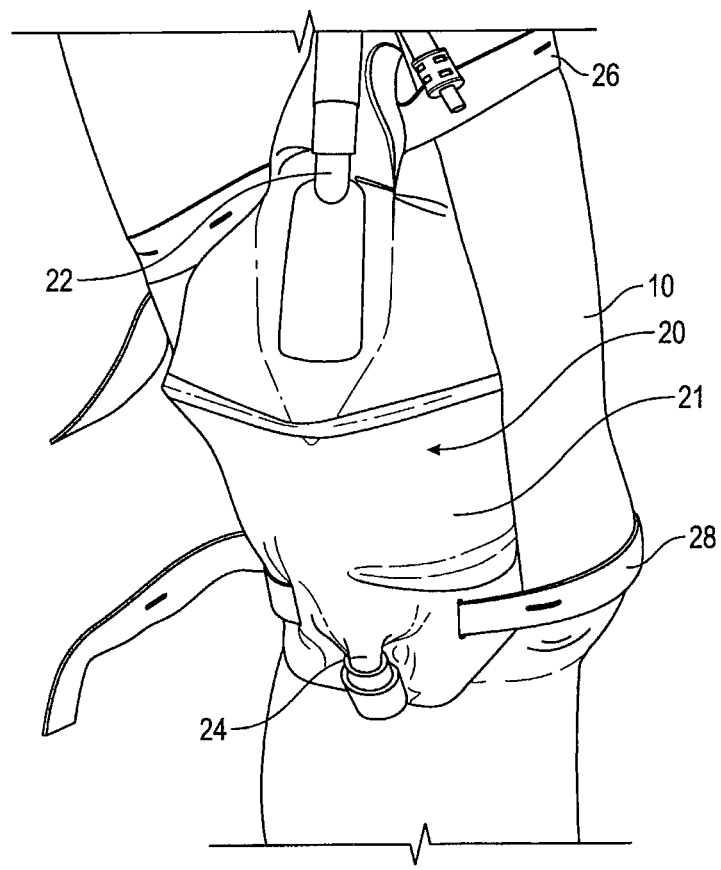
FIG. 1 is a view of a prior art urine collection and drainage device.

Referring to FIG. 1, there is a shown a prior art urine collection and drainage device 20 on a patient's leg 10. Device 20 includes a collection bag 21, an inlet 22, a drain outlet 24 and a pair of straps, upper 26 and lower strap 28. A catheter (not shown) would normally be inserted into the patient's bladder through the urethra, which is then coupled to inlet 22. One disadvantage of this device is that collection bag 21 needs to be emptied from the lower drain outlet 24 requiring the patient to disrobe or pull his pants down in order to reach and activate drain outlet 24. This is more of a challenge if the patient is in a wheelchair or uses a cane or walker.

Figure 2A:
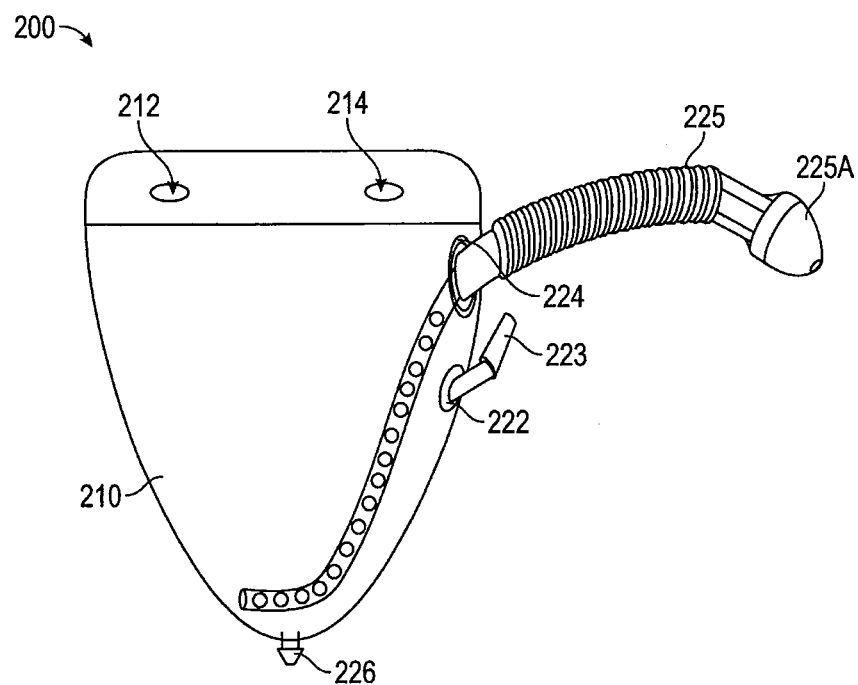
FIG. 2A is a view of an example embodiment of a urine or bodily waste collection system according to the teachings herein.
Figure 2B:
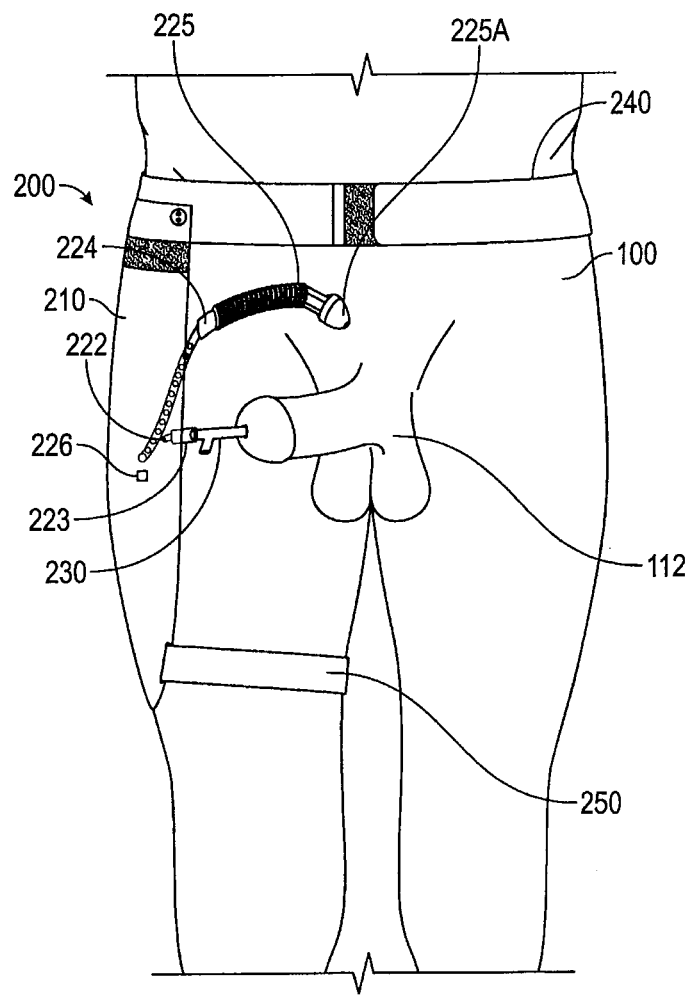
FIG. 2B is a view of an example embodiment of a bodily waste collection and drainage system in use by a male patient according to teachings herein.
Figure 2C:
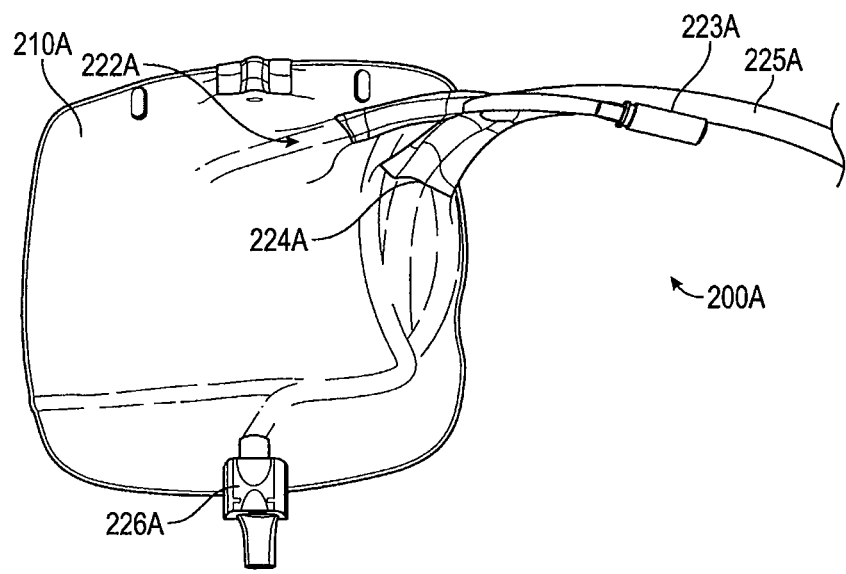
FIG. 2C is another example embodiment of a bodily waste collection and drainage assembly according to the teachings herein.

Referring now to FIGS. 2A-2C, there are described various embodiments of a bodily waste collection and drainage system and device that facilitates emptying or drainage from a standing position of a user or patient. Even if the patient is in a wheelchair or confined to a bed, the bodily waste collection system described herein still allows a patient to conveniently empty the collection bag into a bedpan or it can be used to collect urine samples conveniently from the patient.

Referring particularly to FIGS. 2A and 2B, there are shown views of an example embodiment of a bodily waste collection and drainage system 200 for use by a male patient 100 (detached and attached) according to teachings herein. In a related embodiment, system 200 is configured for use for with a female patient and the embedded catheter is configured for connection with the collection bag (such as in FIG. 2C). In this example embodiment, system 200 includes a collection bag 210, an inlet 222, an outlet 224 and a bottom drain 226. Inlet 222 is coupled to a connector 223 which is coupled to a catheter 230 that is inserted into a patient's urethra (genital area 112) for drainage of urine collected by bag 210. A urine (or other bodily fluid) exit tube 225, having a tip valve 225A, is coupled to outlet 224 for draining or emptying bag 210 through an upper portion of bag 210. Tube 225 has a customizable length with an interior diameter (ID) of about, but not limited to, 0.25 inches. In this example embodiment, tube 225 is comprised of an internal portion 225B (outside bag 210) and an external portion 225C (spanning inside bag 210), with the internal portion 225B having a series of holes 225D (optional) to facilitate drainage and manage internal pressure. In various embodiments, tube 225 is formed from one or more members. Valve 225A can be a twist on/off valve, a push button valve, ball valve, a unidirectional valve, a duck bill or any other valve device that allows for drainage of the collection bag with a substantially immediate shut-off. In a related embodiment, the valve is pressure activated and opens when pressure exerted by the patient on the bag (when trying to empty the bag) exceeds the valve's pressure threshold. In this embodiment, the valve's pressure threshold is configured to be high enough to avoid leakage if incidental or inadvertent pressure is placed on the collection bag.

In this example embodiment, exit tube 225 spans a longitudinal length of bag 210 towards the bottom of the bag to assist in the emptying or draining of the bag. Once the user pulls or extends exit tube 225 and points it towards the toilet (or the urinal if standing up or the bedpan if the patient is in bed or in a wheelchair) and actuates valve 225A, pressure is applied to the bag by the user and then urine or bodily waste is dispelled through tube 225. Waste collection assembly 200 optionally includes a waistband or holster accessory 240 for supporting bag 210 (at loop or holes 212 and 214) and optionally at least one leg strap 250 for strapping bag 210 to a patient's leg. In this example embodiment, bag 210 is formed in a triangular shape to accommodate the user's leg and body contour.

Note that a proximal end of catheter 230 (coming out of patient's urethra) is disposed level to or substantially level to inlet 222 and connector 223 such that a natural drainage level (taking advantage of gravity) is used for the patient's convenience, hence not requiring excessive bladder muscles to push the urine out. Another advantage to this design is that the patient controls the drainage and the emptying of the collection bag versus being forced to empty the entire contents all at once with other prior art devices. The ability to control emptying of the collection bag is useful when circumstances may not permit the patient to empty the entire contents all at once. Another advantage to collection system 200 is that it has two bodily waste exits (tube 225 and drain 226) as compared to prior art systems that just have one exit, just in case one collection bag drainage option fails.

Yet another advantage of the collection bag systems disclosed herein is that collection bag 210 is configured to be positioned along the side of one leg near the waist to be more conducive to the contour of the patient's body and urethral drainage into the bag. In a related embodiment, collection bag 210 is configured to be located in the inside of the patient's leg to help with concealment, such as when a female patient decides to wear a skirt or a male patient prefers to have the collection bags (with associated connectors/connections) on the inside portion of one leg. In yet another embodiment, system 200 is configurable to have two collection bags on both legs for longer use when traveling or when it is not convenient to empty for a number of hours.

Referring now to FIG. 2C, there is shown another example embodiment of a bodily waste collection and drainage assembly 200A according to the teachings herein. System 200A includes a standard rectangular collection bag 210A, with an inlet 222A, an outlet 224A located at the medial aspect of the bag and a bottom drain 226A. Inlet 222A is coupled to a connector 223A which is coupled to a catheter 230 that is inserted into a patient's urethra for drainage of urine collected by bag 210A. An exit tube 225A, having a tip valve 225B, is coupled to outlet 224A for draining or emptying bag 210A through an upper portion of bag 210A. Once the user pulls or extends exit tube 225A and points it towards the toilet (or the urinal if also using it in a standing position) and actuates valve 225A, mild pressure or compression is applied to bag 210A and then urine or waste is dispelled through tube 225A. Once the bag is emptied to the patient's satisfaction, valve 225A is closed and tube 225A is returned to inside the patient's clothing. In a related embodiment, system 200 or 200A or 600 are configurable to include a clip or holder to hold tube 225 securely to bag 210 after use.

In a related embodiment, the collection bag is configured to have an exit tube comprised of an internal portion member that resides inside bag 210 and an external portion member that extends away from the collection bag and is used by the patient for regular bag drainage. Advantages to this embodiment include hygiene within the bag is maintained as the internal portion member of the exit tube stays within the bag while the external portion may be changed by the patient for any reason. In a related embodiment, the internal portion member is permanently coupled to an outlet port connector that in turn is coupled to an interchangeable external portion tube member.

In a yet another example embodiment, bag 210 is configured to have an inlet port and outlet port on the same side of bag or vessel 210 to facilitate flexibility in locating vessel 210 proximate to a patient's bodily fluid drainage orifice (such as a patient's urethra; or abdomen for abdominal drainage or near buttocks for fecal drainage). In this example embodiment, the outlet port is connected to an exit tube member that is extendible through a patient's clothing (pants, shirt, skirt, etc.) thereby facilitating easy drainage without completely disrobing.

In a related embodiment, the collection bag is configurable to only include the upper exit tube without the need for the lower drain tube or drain outlet. This is especially useful where the patient needs a urine collection system with a smaller form factor or wishes to dispose of the unit after it is full. System 200 is configurable for other uses such as a colostomy bag that can be emptied if necessary or used in connection with other drain tubes for bodily fluids wherein the fluid drips or drains out with or without gravitational forces.

Figure 3A:
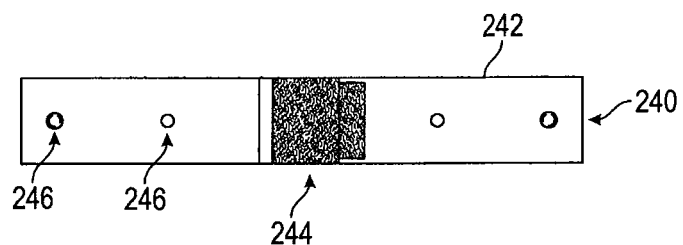
FIGS. 3A-3B are views of a waistband accessory for a bodily waste collection device as taught herein.
Figure 3B:
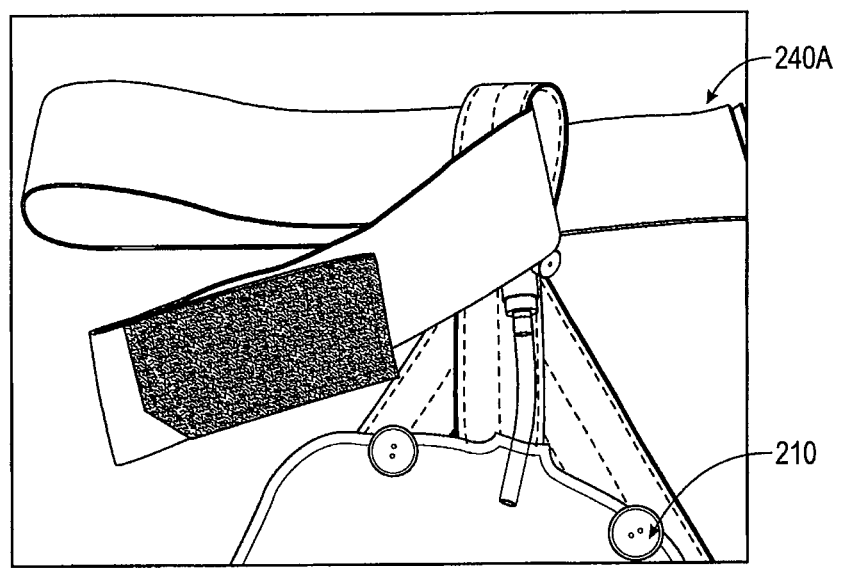

Referring now to FIGS. 3A-3B, there is a view of a waistband member or assembly 240 for a collection device as taught herein. In particular, member 240 includes a band 242 that includes a fastener assembly 244 at both ends. Fastener assembly 244 includes, but is not limited to, a hook and loop (Velcro®) arrangement, a snap button, and a button and button hole. Waistband member 240 includes connection members 246 for supporting bags 210, 210A, 410, 510, and 610.

In a related embodiment, the collection bag is supported in the pelvic area (near the urethra) by providing a spandex-type leg cuff, sleeve or band member (which can also be in the form of a band with a hook and loop or simply a hook fastener, depending on the band material chosen, that is wrapped around the appendage) that is pulled up to the thigh and that has an additional external pocket/sleeve that allows the patient to slip the collection bag down into it. The spandex cuff or sleeve or band member (or other elastic-type material) can have a side slit to accommodate the Foley connection (from the catheter in urethra) and a lower slit to accommodate the bottom drain. In an alternative embodiment, the sleeve (or cuff or band) is on the inside of the leg so that it is between the legs instead of on the side of the leg.

The side sleeve/pocket can also be large enough to accommodate a plate member (plastic or other rigid/semi-rigid) that serves as a back plate to the bag to allow the user to press the collection bag or vessel against it for additional leverage. Another advantage to this feature is that in instances where patients have difficulty applying pressure to the bag, the sleeve or cuff or band member can act as the source for producing back pressure within the collection bag as it fills with urine. The level of back pressure, which would be advantageous for bag drainage, can be determined by the denier and compliance of the sleeve or cuff.

Figure 4:
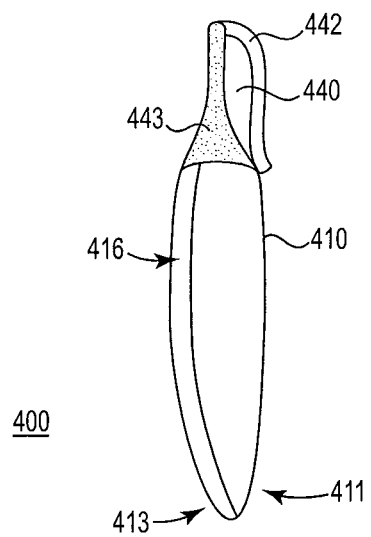
FIG. 4 illustrates a side view of a waste collection bag as taught herein.

Referring now to FIG. 4, there is shown a side view of an example urine collection bag assembly 400 according to the teachings herein. Bag assembly 400 includes a bag portion 410, with a belt loop assembly 440, and a backing plate 416. Belt loop assembly 440 includes a belt loop member 442 and a rear loop support 443, both of which support bag 410 near the lower pelvic (or genital) area of a patient. Backing plate 416, in this example embodiment, is either rigid or semi-rigid to provide a surface against a backside 413 of bag 410 to assist the user (during compression) in emptying or draining the bag, as pressing the bag only against the user's leg during draining may be inefficient or time consuming. In one example embodiment, a waistband assembly used to support bag 410 near the patient's lower pelvic area is equipped with backing plate 416. In a related embodiment, bag 410 includes a thicker layer of polyolefin (or PTFE or ePTFE), polyethelyene, polypropylene material or the like to assist in compression of bag 410 by the patient. In yet another related embodiment, backing plate 416 is substituted with a spun polymer sheet fabric or felt-like surface to promote airflow between the leg skin and collection bag 410. In various embodiments, bag 410 has a volume of about 400 ml-800 ml and a configuration that is tapered in the direction away from belt loop assembly 440.

Figure 5:
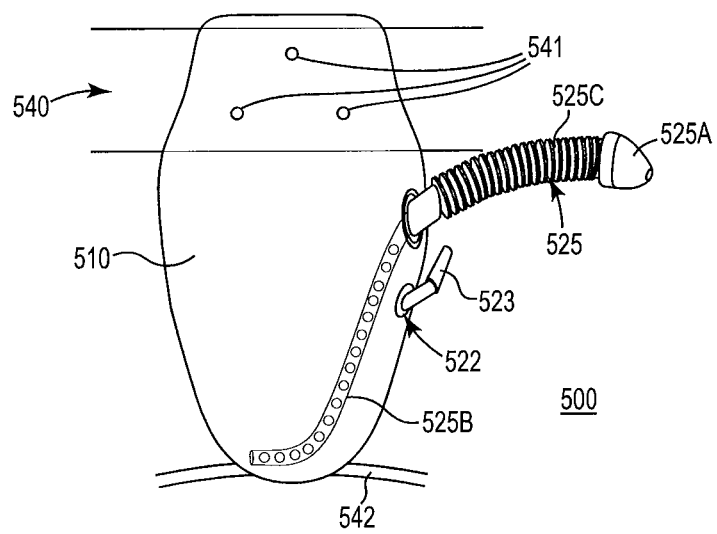
FIG. 5 illustrates a front view of another waste collection bag as taught herein.

Referring now to FIG. 5, there is shown a front view of another example collection assembly 500 which includes a bag portion 510, with a portion of a belt holding assembly 540 (and retaining buttons 541) and a lower retaining leg strap 542. Similar to collection assembly 200, assembly 500 includes an inlet 522 with associated connector 523 to connect to a Foley catheter, an outlet 524 with a catheter 525 located there through. Catheter 525 is comprised of an internal portion 525B (with optional holes 525D), an external portion 525C and an end portion/cap with a valve 525A. In this example embodiment, inlet 522 is equipped with a unidirectional flow valve (or duck valve) in the rear (or inside of bag) to prevent bodily waste or urine from flowing retrograde back towards the patient's catheter and thus the patient's bladder.

Figure 6:
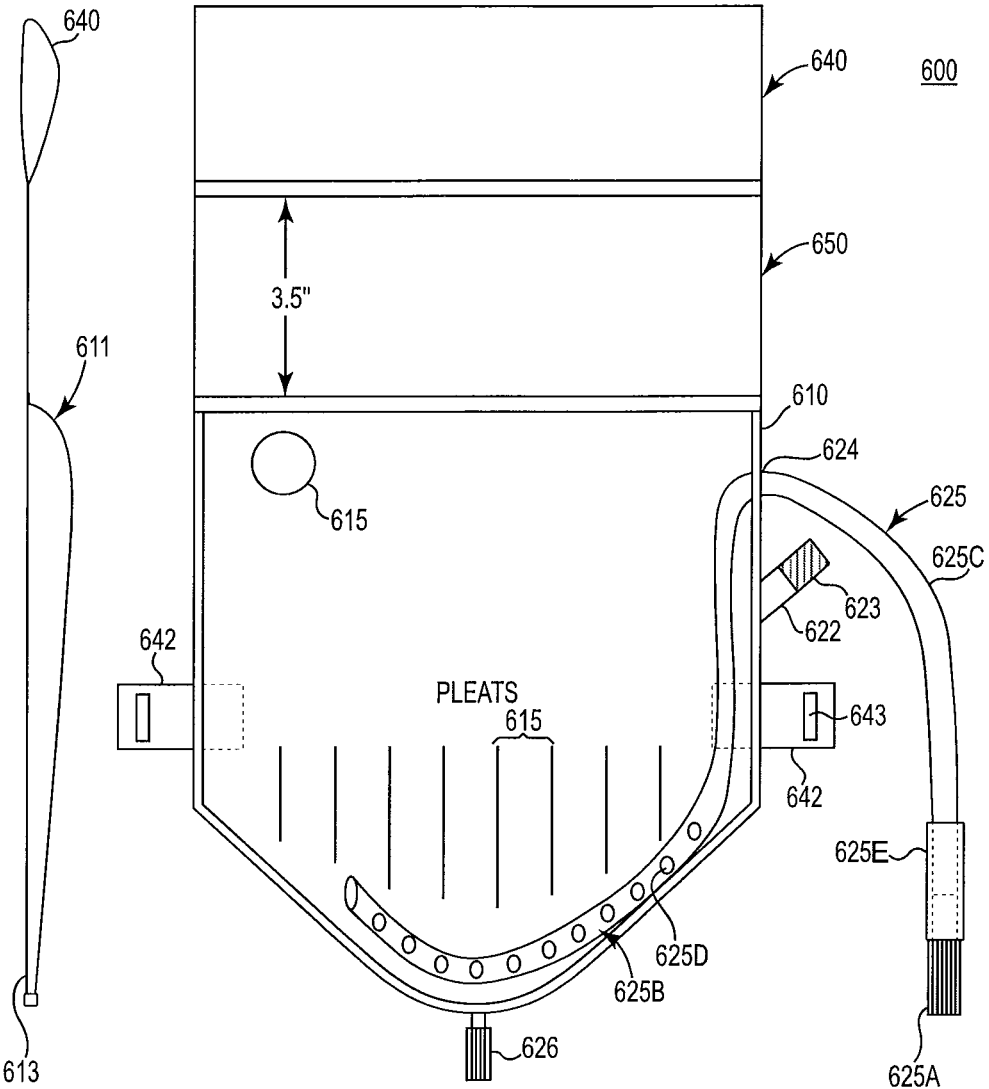
FIGS. 6A and 6B illustrate front and side views of another bodily waste collection assembly as taught herein.

Referring now to FIGS. 6A and 6B, there are shown front and side views of another example embodiment of a bodily waste collection and drainage system 600 for use by a male patient according to teachings herein. In a related embodiment, system 600 is configurable for use by a female patient and the embedded catheter is configured for connection with the collection bag. In this example embodiment, system 600 includes a collection bag 610, a belt loop assembly portion 640 with a spacer member 650, which provides some distance between collection bag 610 and loop assembly 640, thereby allowing bag 610 to be suspended near the patient's lower pelvic area (close to a urethral catheter). In this example embodiment, seal lines are formed between various sections to strengthen the assembly while creating some space for hygiene for the patient. For example, a seal line 641 is located between belt loop assembly 640 and spacer member 650. A seal line 651 is located between spacer member 650 and bag 610. A side view of assembly 600 (FIG. 6B) is lined up with the front view and shows loop 640, spacer member 650, a front 611 of bag 610 and a rear 613 of bag 610.

In this example embodiment, bag 610 includes an ePTFE (or other such material which acts as a one way vent) vent 615, an inlet 622, an outlet 624 and a bottom drain 626 with a cleanout valve. Inlet 622 is coupled to a connector 623 which is coupled to a catheter 630 (not shown) that is inserted into a patient's urethra for drainage of urine collected by bag 610. A urine (or other bodily fluid) exit tube 625, having a tip valve 625A, is coupled to outlet 624 for draining or emptying bag 610 through an upper portion of bag 610. In this embodiment, catheter 625 is comprised of an internal portion 625B (with optional holes 625D), an external portion 625C, an outer diameter tube 625E, and an end portion/cap with a valve 625A. Valve 625A can be a twist on/off valve; a push button valve; ball valve, unidirectional valve, duck bill valve or any other valve device that allows for drainage of the collection bag with a substantially immediate shut-off. In a related embodiment, the valve is pressure activated and opens when pressure exerted by the patient on the bag (when trying to empty the bag) exceeds the valve's pressure threshold. In this embodiment, the valve's pressure threshold is configured to be high enough to avoid incidental or inadvertent outflow due to pressure placed on the collection bag.

In this example embodiment, exit tube 625 spans a longitudinal length 625B of bag 610 towards the bottom of the bag to assist in the emptying or draining of the bag. Once the user pulls or extends exit tube 625 and points it towards the toilet (or the urinal if also standing up or the bedpan if the patient is in bed or in a wheelchair) and actuates valve 625A, pressure is applied to the bag by the user and then urine or bodily waste is dispelled through tube 625. Waste collection assembly 600 optionally includes a waistband or holster accessory that couples to belt loop assembly 640 for supporting bag 610 and at least one leg strap 650 for strapping bag 610 to a patient's leg. In this example embodiment, bag 610 is formed in a triangular or upside flask shape to accommodate the user's leg and body contour.

In use, the patient's indwelling catheter is disposed level or substantially level to inlet 622 and connector 623 such that natural drainage (e.g., gravity) is used for the patient's convenience, hence not requiring excessive bladder muscles to push the urine out (or up to a bag as in the prior art). Another advantage to this design is that the patient controls the drainage and the emptying of the collection bag versus being forced to empty the entire contents all at once with other prior art devices. The ability to control emptying of the collection bag is useful when circumstances may not permit the patient the empty the entire contents all at once. Other advantages to this collection system are similar to that described above. Collection bag 610 also includes a set of pleats (baffles) 618 to facilitate drainage. Catheter tube device 625, in various example embodiments is customizable in length, is formed from various materials including a corrugated or ribbed material and has an internal diameter (ID) large enough (for example 0.25 inches) to facilitate drainage and keep internal pressure to a minimum.

An example of the components and materials used in the various collection systems describe herein include:

| Mfgr. And PN | Description |
| --- | --- |
| Qosina: 80041 p. 172 | Tube End Drain Valve, Bag Cleanout and Drain Line |
| Qosina: 94617 p. 167 | Urinary Connector, 1-way, Foley Connection |

-continued

| Mfgr. And PN | Description |
| --- | --- |
| Qosina: DEPH Free PVC Class IV | Bag Drain Tube ¼" × ⅜" |
| Qosina: DEPH Free PVC Class IV | Bag Clean Out Tube 0.280" × 0.400' Elastic Waist Band w/Velcro tab, 1.5" × 30" Elastic Leg Strap w/Velcro tab, 1.0" × 30" |
| Bag, Back, 8 mil Polyolefin sheet | Thicker bag backing |
| Bag Front, 3 mil Polyolefin sheet, | Thinner bag face |
| Leg Strap tab, 8 mil polyolefin sheet | Heat bonded to receive waistband |

The various collection bags described herein are made from any one of, or a combination of, materials: PTFE, expanded PTFE, and PTFE composites, which provide airflow and liquid resistance for vented containers. When integrated into a package design, ePTFE allows for the inflow of gases such as air without allowing liquid to penetrate the venting membrane and subsequently permeate out of the collection bag as internal pressure builds. When liquid penetrates other porous material, airflow stops. This phenomenon is referred to as "wetting out". Ordinary membranes that simply allow initial airflow will clog quickly, prohibiting consistent airflow and will often leak—especially when a container is in an upside down position during use. Packaging vents, such as vent 615, allow consistent airflow, even after liquid contact. When liquids are sprayed or dispensed, a vacuum is created within a closed system. These packaging vents allow the package to breathe by equalizing pressure. This simple closure vent solution helps to assure that containers maintain their shape and do not leak while liquids are being dispensed.

Figure 7:
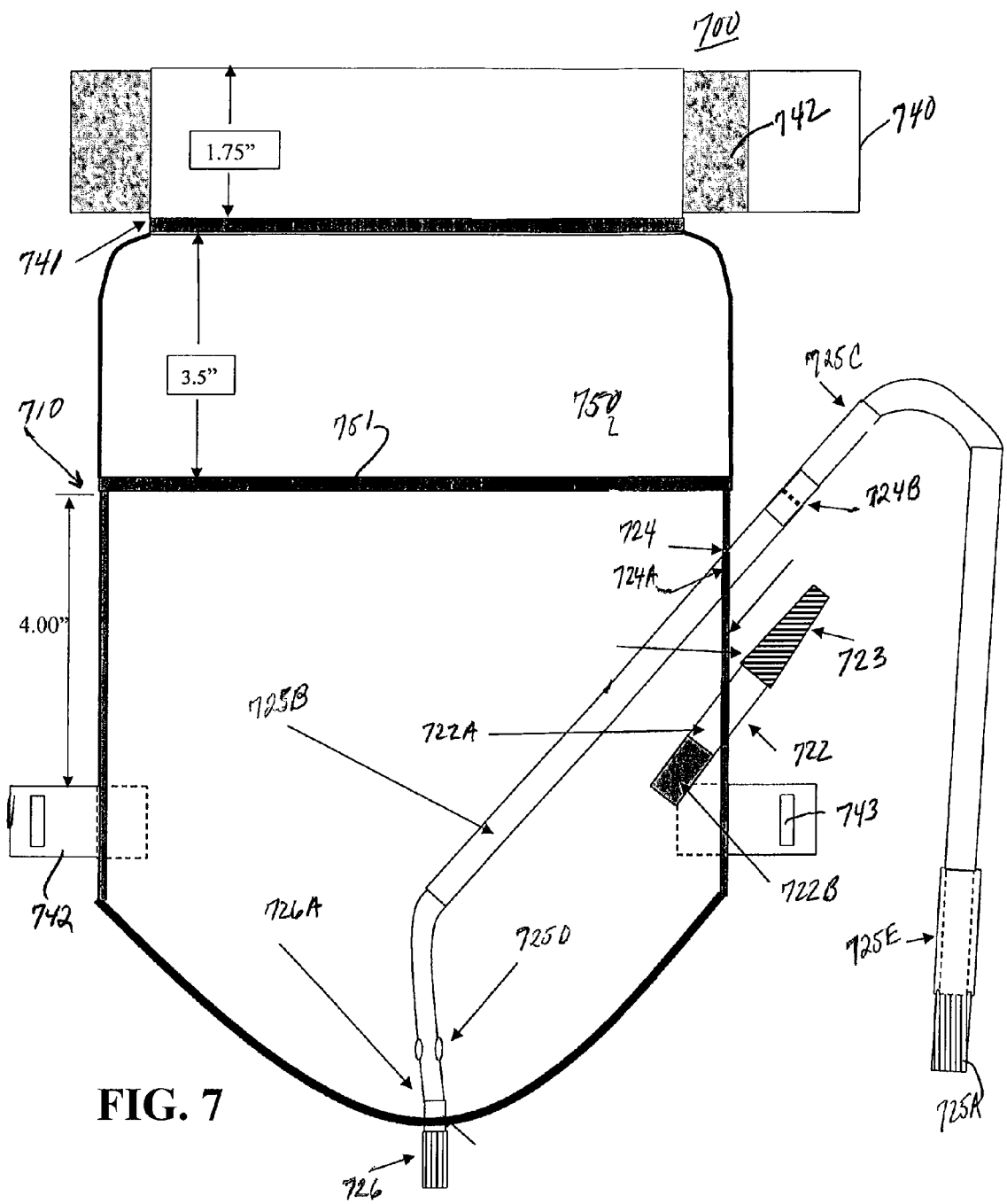
FIG. 7 illustrates a front view of yet another bodily waste collection assembly as taught herein.

Referring now to FIG. 7, there is shown a front view of yet another example embodiment of a bodily waste collection and drainage system 700 for use by a male patient according to teachings herein. In a related embodiment, system 700 is configurable for use by a female patient and an embedded catheter is configured for connection with the collection bag. In this example embodiment, system 700 includes a collection bag 710, a belt loop assembly portion 740 with a fastener 742 with a spacer member 750, which provides some distance between collection bag 710 and loop assembly 740, thereby allowing bag 710 to be suspended near the patient's lower pelvic area (close to a urethral catheter). In this example embodiment, seal lines are formed between various sections to strengthen the assembly while creating some space for hygiene for the patient. For example, a seal line 741 is located between belt loop assembly 740 and spacer member 750, while another seal line 751 is located between spacer member 750 and bag 710.

In this example embodiment, bag 710 includes (optionally an ePTFE vent or other such material which acts as a one way vent) an inlet 722 and a duck bill or unidirectional flow valve 722A; an outlet 724, outlet weld 724A and a connector 724B; and a bottom drain joint 726A with a cleanout valve 726. Inlet 722 (which may also have a weld connected to the side of the bag for stability) is coupled to a connector 723 which is coupled to a catheter 730 (not shown) that is inserted into a patient's urethra for drainage of urine collected by bag 710. A urine (or other bodily fluid) exit tube 725, having a tip valve 725A, is coupled to outlet 724 for draining or emptying bag 710 through an upper portion of bag 710. In this embodiment, catheter 725 is comprised of an internal portion 725B (with optional one or two infeed holes 725D), an external portion 725C, an outer diameter tube 725E, and an end portion/cap with a valve 725A. Valve 725A can be a twist on/off valve; a push button valve; ball valve, unidirectional valve, duck bill valve or any other valve device that allows for drainage of the collection bag with a substantially immediate shut-off. In a related embodiment, the valve is pressure activated and opens when pressure exerted by the patient on the bag (when trying to empty the bag) exceeds the valve's pressure threshold. In this embodiment, the valve's pressure threshold is configured to be high enough to avoid incidental or inadvertent outflow due to pressure placed on the collection bag.

An example of the components and materials used in the various collection systems describe herein include:

| Description | Material |
| --- | --- |
| State Narrow Fabric Strap-Waist (Skin Contact) | White Plush Latex Free |
| State Narrow Fabric Strap-Leg (Skin Contact) | White Plush Latex Free |
| Velcro PSA Hook | Velcro, Nylon with RF Adhesive |
| Leg Strap w/1.5 × 0.375" Slit | PVC, (DEHP Free) |
| Input Port (Tube) for Mandrel (Urine Contact) | PVC tube (DEHP Free) |
| Duckbill Valve (Urine Contact) | PVC valve, Seal on Edge |
| Input Connector | Urinary Connector PC |
| Output Port (Tube) for Top/Bottom Mandrel w/¼" Drain Holes | PVC Tube (DEHP Free) |
| Output Port (Tube) for Cushion | PVC Tube (DEHP Free) |
| Output Port Connector for Tube | HDPE Tube |
| Drainage Valve | PVC Tube End Drain Valve, Twist Control |
| Tactile Cushion (Skin Contact) | Drain Tube Cushion |
| Back Sheet 1 (Skin Contact) | PVC, losy Sontara (DEHP Free) |
| Back Sheet 2 | PVC (DEHP Free) |
| Top Sheet | PVC (DEHP free) |

In this example embodiment, exit tube 725 spans an almost longitudinal length 725B of bag 710 towards the bottom of the bag (including an upright section attached to the drain valve with holes 725D to facilitate siphoning of the fluids) to assist in the emptying or draining of the bag. In this configuration, internal tube 725B is fixed to the apex or bottom of the vessel on one end and is affixed at the other end the outlet connector, thereby avoiding kinking of the tube or blocking of infeed holes 725D (holes are about 0.25 inches in diameter). One of the advantages of this configuration is that the urine or bodily fluid pressure builds at the bottom of the vessel as the bag fills and therefore holes 725D are located at the highest pressure points within the bag. Once the user applies initial compression to empty the bag or vessel, hydraulic pressure will quickly build up within tube 725B at the bottom so that the fluid flows over the peak curve in the drain tube portion external to the bag and will start emptying the bag automatically and without further compression. In other prior art configurations, the use of Y or T connectors to connect the inlet and outlet to the same internal drain tube or to connect to only one port, by which both the inlet and outlet tubes are connected, although arguably cost effective due to less parts being used in the device, the connectors and shared inlet/exit tubes actually lower the pressure at the bottom of the collection bag making it more difficult for the user to empty the bag contents and to try to initiate the siphoning or emptying action. In other prior art configurations, only using interior tube or the drainage tube and valve at the bottom of the bag (each of which may not be not secure and subject to movement or kinking) makes draining the bag through the upper drainage tube dependent on the interior diameter of the drainage tube opening and the expectation of minimal movement of the unsecured tube end within the bag or collection vessel.

Once the user pulls or extends exit tube 725 and points it towards the toilet (or the urinal if also standing up or the bedpan if the patient is in bed or in a wheelchair) and actuates valve 725A, pressure is initially applied to the bag by the user and then urine or bodily waste is expelled through tube 725 once the siphoning action commences (after which the user no longer needs to exert any pressure as the bag empties itself). In this example embodiment, the combination of the upright configuration of the tube near the drain valve along with the infeed holes on the sidewall facilitate the creation of the siphoning action to empty the vessel. Waste collection assembly 700 optionally includes a waistband or holster accessory that couples to belt loop assembly 740 for supporting bag 710 and at least one leg strap 750 for strapping bag 710 to a patient's leg. In this example embodiment, bag 710 is formed in a triangular or upside flask (or chevron) shape to accommodate the user's leg and body contour as well as to concentrate the bodily fluid (and pressure) closer to the drain tube and infeed holes 725D.

In use, the patient's indwelling catheter is disposed level or substantially level to inlet 722 and connector 723 such that natural drainage (e.g., gravity) is used for the patient's convenience, hence not requiring excessive bladder muscles to push the urine out (or up to a waist bag as in the prior art). Another advantage to this design is that the patient controls the drainage and the emptying of the collection bag versus being forced to empty the entire contents all at once with other prior art devices. The ability to control emptying of the collection bag is useful when circumstances may not permit the patient to empty the entire contents all at once. Other advantages to this collection system are similar to that described above. Catheter tube device 725, in various example embodiments is customizable in length, is formed from various materials and has an internal diameter (ID) large enough (for example 0.25 inches) to facilitate drainage and keep internal pressure to a minimum. Various embodiments described herein are operable with different types of catheters including, but not necessarily limited to, Foley and condom or urisheath catheters.

The following patents and publications are herein incorporated by reference in their entireties: U.S. Pat. Nos. 5,002,541; 5,618,277; 6,007,521; 7,160,276; 7,931,630 and 8,002,766.

While the various embodiments of the invention have been described above in terms of specific embodiments, it is to be understood that the invention is not limited to these disclosed embodiments. Upon reading the teachings of this disclosure, many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

What is claimed is:

1. A catheter device accessory assembly for urine collection of a patient comprising:
   a unitary urine collection vessel having an upper portion and a lower portion,
   an inlet port disposed on said unitary urine collection vessel and configured to be coupled to a connector, the connector adapted to be connected to a catheter device;
   an outlet port disposed on the upper portion of said unitary urine collection vessel and disposed separate and above said inlet port, said outlet port having an external side and an internal side; and
   a drainage tube assembly comprising an external tube portion and an internal tube portion, said external tube portion coupled to the external side of said outlet port and adapted to extend away from said unitary collection vessel for external drainage, said internal tube portion coupled to the internal side of said outlet port and adapted to extend internally from said outlet port within and into the lower portion of said collection vessel, a distal end of said internal tube portion in operative contact with a floor or bottom of the collection vessel, wherein the internal tube has at least one hole in a sidewall of the tube spaced from said distal end of said internal tube portion with the sidewall hole being located adjacent the bottom of the collection vessel;
   wherein said collection vessel is configured to be emptied through said drainage tube assembly upon initial compression of the lower portion of the collection vessel, thereby commencing a siphoning action.

2. The catheter accessory device of claim 1, wherein the unitary urine collection vessel is adapted to be emptied by the patient in a standing position with said external tube portion extended away from said collection vessel for external drainage.

3. The catheter accessory device of claim 1, wherein said external tube portion of the drainage tube comprises a valve member for selectively draining said urine collection vessel and wherein the outlet port includes a weld as a stop mechanism to prevent the outlet port from being pulled out of the urine collection vessel.

4. The catheter accessory device of claim 1, further comprising a waistband attachment assembly adapted to support said collection vessel on a user's body such that said inlet port is adjacent a proximal end of a catheter located in a patient's urethra.

5. The catheter accessory device of claim 4, wherein said waistband assembly further comprises a leg band member configured to secure said collection vessel to a patient's leg.

6. The catheter accessory device of claim 4, further comprising a spacing gap member located between the waistband assembly and the upper portion of the collection vessel, the spacing gap configured to house the non-extended external tube portion.

7. The catheter accessory device of claim 1, wherein a front panel of said collection vessel is configured to be compressed against an equally sized stiffened rear panel of said unitary collection vessel to improve collection vessel external drainage with said external tube portion extended away from said collection vessel.

8. The catheter device assembly of claim 1, wherein the urine collection vessel includes a vent on an upper portion of the vessel.

9. A catheter accessory device for collecting urine from a patient comprising:
   a urine collection vessel having an upper and lower portions and configured to be supported by the patient's waist or leg;
   an inlet port coupled to the urine collection vessel the inlet port having a connector adapted to be coupled to a catheter;
   an outlet port disposed in the upper portion of and coupled to the urine collection vessel, the outlet port coupled to a drainage tube member that is adapted to extend above the inlet port and away from the collection vessel, an internal portion of the drainage tube member extending within and to a bottom of the urine collection vessel and an external portion of the drainage tube member comprising a valve for selectively draining the urine collection vessel; and
   a drain valve coupled to the bottom of the urine collection vessel and coupled at another end with the internal portion of the drainage tube member, the internal portion of the drainage tube being disposed in an upright configuration from the drain valve and including at least one hole in a sidewall near the drain valve, the least one sidewall hole being located adjacent the bottom of the collection vessel;
   wherein the urine collection vessel is adapted to be emptied through said drainage tube member when the patient is in a standing position by initially compressing the vessel until a siphoning action commences.

10. A bodily fluid collection system for use by a patient comprising:
    a unitary collection vessel configured to have an inlet port and an outlet port, said inlet port disposed proximate to a patient's drainage orifice when the collection system is in use, wherein drainage from the orifice occurs gravitationally;
    a bodily conduit member configured to be coupled to said inlet port and configured to be coupled to the patient's drainage orifice; and
    a drainage conduit member configured to be coupled to said outlet port and adapted to extend from said collection vessel for external drainage of said collection vessel, wherein a portion of said drainage conduit member extends internally into and within said collection vessel and extends below said inlet port and wherein a distal end of said drainage conduit member is in operative contact with a floor or bottom of the collection vessel, the drainage conduit member having at least one hole in a sidewall that is spaced from the distal end of said drainage conduit member, with the at least one sidewall hole being located below the inlet port of the collection vessel;
    wherein said collection vessel is configured to be emptied through said drainage conduit member upon initial compression of the lower portion of the collection vessel, thereby commencing a siphoning action.

11. The bodily fluid collection system of claim 10, wherein said bodily conduit member comprises a catheter.

12. The bodily fluid collection system of claim 10, further comprising an attachment assembly configured to support said collection vessel about a patient's waist.

13. The bodily fluid collection system of claim 12, wherein said attachment assembly is configured to support said collection vessel about a patient's leg.

14. The bodily fluid collection system of claim 12, further comprising a spacing gap member located between the attachment assembly and an upper portion of the collection vessel, the spacing gap configured to house a non-extended drainage conduit member.

15. The bodily fluid collection system of claim 10, further comprising an attachment assembly configured to support said collection vessel about a patient's leg.

16. The bodily fluid collection system of claim 10, wherein a front panel of said collection vessel is configured to be compressed against an equally sized stiffened rear panel of said unitary collection vessel to improve collection vessel external drainage with said external tube portion extended away from said collection vessel.

17. The bodily fluid collection system of claim 1, wherein the inlet port includes a unidirectional flow valve to prevent fluids from flowing out through the inlet port.

18. The catheter device assembly of claim 1, wherein the urine collection vessel includes a clip or clamp member to secure the drainage tube assembly when not in use.

19. The catheter device assembly of claim 1 wherein the urine collection vessel includes at least one baffle within the vessel adapted for ease of drainage.

20. A catheter device accessory assembly for urine collection of a patient comprising:
   a urine collection vessel having an upper portion and a lower portion, said collection vessel having a longitudinal axis along a length of said collection vessel;
   an inlet port disposed on said urine collection vessel and configured to be coupled to a connector, the connector adapted to be connected to a catheter device;
   an outlet port disposed on the upper portion of said urine collection vessel and disposed separate and above said inlet port, said outlet port having an external side and an internal side; and
   a drainage tube assembly comprising an external tube portion and an internal tube portion, said external tube portion coupled to the external side of said outlet port and adapted to extend away from said collection vessel for drainage, said internal tube portion coupled to the internal side of said outlet port and adapted to extend from said outlet port and internally into the lower portion of said collection vessel, a distal end of said internal tube portion being disposed substantially upright and substantially parallel with the longitudinal axis and being coupled to a lower drain valve member located at a floor or bottom of said collection vessel, wherein the internal tube portion has at least one hole in a sidewall of the tube spaced from said distal end of said internal tube portion with the sidewall hole being located adjacent the bottom of the collection vessel;
   wherein said collection vessel is configured to be emptied through said drainage tube assembly upon initial compression of the lower portion of the collection vessel, thereby commencing a siphoning action.

21. The catheter accessory device of claim 20, wherein the urine collection vessel is adapted to be emptied by the patient in a standing position with said external tube portion extended away from said collection vessel.

22. The catheter accessory device of claim 20, further comprising a waistband attachment assembly adapted to support said collection vessel on a patient's body such that said inlet port is adjacent a proximal end of a catheter located in a patient's urethra.

23. The catheter accessory device of claim 22, wherein said waistband assembly further comprises a leg band member configured to secure said collection vessel to a patient's leg.

24. The catheter accessory device of claim 22, further comprising a spacing gap member located between the waistband assembly and the upper portion of the collection vessel, the spacing gap configured to house the non-extended external tube portion.

* * * * *